(12) United States Patent
Hu et al.

(10) Patent No.: US 8,377,932 B2
(45) Date of Patent: Feb. 19, 2013

(54) PREPARATION OF 1-(SUBSTITUTED BENZYL)-5-TRIFLUOROMETHYL-2(1H)PYRIDONE COMPOUNDS AND SALTS THEREOF AND THEIR APPLICATIONS

(75) Inventors: Gaoyun Hu, Changsha (CN); Lijian Tao, Changsha (CN); Jun Chen, Changsha (CN)

(73) Assignee: Central South University, Changsha (CN)

( * ) Notice: Subject to any disclaimer, the term of this patent is extended or adjusted under 35 U.S.C. 154(b) by 0 days.

(21) Appl. No.: 13/322,153

(22) PCT Filed: May 24, 2010

(86) PCT No.: PCT/CN2010/073131
§ 371 (c)(1),
(2), (4) Date: Feb. 8, 2012

(87) PCT Pub. No.: WO2010/135976
PCT Pub. Date: Dec. 2, 2010

(65) Prior Publication Data
US 2012/0129859 A1 May 24, 2012

(30) Foreign Application Priority Data

May 25, 2009 (CN) .......................... 2009 1 0043502

(51) Int. Cl.
| | | |
|---|---|---|
| *A61K 31/5377* | (2006.01) | |
| *A61K 31/497* | (2006.01) | |
| *A61K 31/4427* | (2006.01) | |
| *A61K 31/44* | (2006.01) | |
| *C07D 413/02* | (2006.01) | |
| *C07D 401/02* | (2006.01) | |
| *C07D 211/06* | (2006.01) | |
| *C07D 211/80* | (2006.01) | |

(52) U.S. Cl. ................ 514/235.5; 514/253.12; 514/318; 514/345; 544/131; 544/360; 546/255; 546/290

(58) Field of Classification Search ............... 514/235.5, 514/253.12, 318, 345; 544/131, 360; 546/255, 546/290
See application file for complete search history.

(56) References Cited

FOREIGN PATENT DOCUMENTS

| | | |
|---|---|---|
| CN | 1646125 A | 7/2005 |
| CN | 1878757 A | 12/2006 |
| CN | 101235030 A | 8/2008 |
| CN | 101237869 A | 8/2008 |
| CN | 101371833 A | 2/2009 |
| WO | WO-2005009392 A2 | 2/2005 |
| WO | WO-2006122154 A2 | 11/2006 |
| WO | WO-2007/053685 A2 | 5/2007 |
| WO | WO-2007/062167 A2 | 5/2007 |
| WO | WO-2008154207 A1 | 12/2008 |
| WO | WO-2009149188 A1 | 12/2009 |
| WO | WO-2010/085805 A1 | 7/2010 |
| WO | WO-2010/135470 A1 | 11/2010 |

OTHER PUBLICATIONS

Database Accession No. 339024-94-1, Chemical Abstracts Service, Columbus, Ohio, XP-002684268, May 30, 2001.
Database Accession No. 764691-46-5, Chemical Abstracts Service, Columbus, Ohio, XP-002684269, Oct. 18, 2004.
Database Accession No. 768724-02-5, Chemical Abstracts Service, Columbus, Ohio, XP-002684270, Nov. 23, 2004.
Database Accession No. 685542-68-1, Chemical Abstracts Service, Columbus, Ohio, XP-002684271, May 25, 2004.
Extended European Search Report dated Oct. 12, 2012, issued in corresponding European Application No. 10780057.5.

*Primary Examiner* — Samantha Shterengarts
(74) *Attorney, Agent, or Firm* — Birch, Stewart, Kolasch & Birch, LLP (57) ABSTRACT

1-(substituted benzyl)-5-trifluoromethyl-2(1H)pyridone compounds and their pharmaceutical acceptable salts are disclosed. The preparation methods of the compounds and their salts and the use of the same for preparing the medicaments for treating fibrosis are also disclosed. New pyridine compounds and their salts are obtained from trifluoromethyl pyridone as starting material.

6 Claims, 1 Drawing Sheet

PREPARATION OF 1-(SUBSTITUTED BENZYL)-5-TRIFLUOROMETHYL-2(1H)PYRIDONE COMPOUNDS AND SALTS THEREOF AND THEIR APPLICATIONS

This Application is a U.S. National Phase of the International Application No. PCT/CN2010/073131 filed on 24 May 2010 designating the U.S. and published on 2 Dec. 2010 as WO 2010/135976.

TECHNICAL FIELD

The invention relates to 1-(substituted benzyl)-5-trifluoromethyl-2(1H)pyridone compounds, preparation methods and medical applications for the same.

BACKGROUND OF THE INVENTION

In a variety of organs or tissues, fibrosis causes reduction of parenchyma cells therein and an increase of fibrous connective tissues, eventually damaging tissue structures, causing tissue dysfunction or even organ failure. The mechanism of fibrosis, and diagnostic methods and prevention measures for fibrosis of organs or tissues have been widely studied. In prior art, considerable progress has been made in some aspects, but some key unresolved issues still exist.

U.S. Pat. No. 3,839,346A, U.S. Pat. No. 4,052,509A, U.S. Pat. No. 4,042,699 disclose 29 pyridone compounds having structural formula I as follows,

Structural formula I and disclose functions of the pyridone compounds of resisting inflammation, allaying fever, reducing the level of serum uric acid, relieving pain or the like, wherein 5-methyl-1-phenyl-2(1H)-pyridone (Pirfenidone, PFD) has the best activity and lower toxicity.

U.S. Pat. No. 5,310,562 discloses 5-methyl-1-phenyl-2(1H)-pyridone for the first time in 1994, that is Pirfenidone (PFD), having an anti-fibrosis biological activity; subsequently U.S. Pat. Nos. 5,518,729 and 5,716,632 disclose N-substituted-2-(1H)pyridone described as the structural formula I and N-substituted-3-(1H)pyridone having the same anti-fibrosis function. Forty-four compounds are specified, most of which are known compounds derived from U.S. Pat. No. 4,052,509; and in the compounds, R1, R2, R3, and R4 are defined as methyl groups or ethyl groups.

Pirfenidone (PFD) is proven to have effectiveness in fibrosis prevention through in vitro and animal experiments. Pirfenidone has functions of stopping or even converting ECM accumulation and preventing or reversing fibrosis and scar formation in experiments using animals with renal fibrosis and pulmonary fibrosis and in the clinical treatment of patients with idiopathic pulmonary fibrosis (Shimizu T, Fukagawa M, Kuroda T, et al. Pirfenidone prevents collagen accumulation in the remnant kidney in rats with partial nephrectomy. Kidney Int, 1997, 52 (Suppl 63): S239-243; Raghu G, Johnson W C, Lockhart D, et al. Treatment of idiopathic pulmonary fibrosis with a new antifibrotic agent, pirfenidone. Am J Respir Crit Care Med, 1999, 159: 1061-1069).

The applicant proposes a CN patent ZL02114190.8 and provides a class of pyridone compounds of the structural formula II.

Structural formula II

In structural formula II, if n=1, the substituent R is F, Br, or I; if n=2, the substituents R are F, Cl, Br, I, a saturated linear alkyl group, an oxo-substituted saturated linear alkyl group, or a halo-substituted saturated linear alkyl group.

The substituent R is at any of the ortho-position, meta-position, and para-position on a benzene ring.

Pirfenidone has come into the market in Japan in 2008 for treating indications for pulmonary fibrosis. However, Pirfenidone and its derivatives do not have high enough strength. The clinical dose of Pirfenidone achieves 2400 mg/day.

Patent publications WO2007053685 and WO2006122154 disclose compounds having functions of inhibiting p38 kinase, applied to treatment of fibrosis diseases and disclose the structural formula III;

Structural formula III wherein, R1-R4 each are H, alkyl, substituted allyl, alkenyl, haloalkyl, nitroalkyl, hydroxyalkyl, alkoxyl, phenyl, substituted phenyl, halogen, hydroxyl, alkoxyalkyl, carboxyl, alkoxycarbonyl, etc.; X1-X5 each are H, halogen, an alkoxyl group, or a hydroxyl group.

WO2007062167 also discloses compounds having functions of inhibiting p38 kinase and applied to treatment of various fibrosis diseases, wherein some structures are shown as follows:

Some simple substituents are provided on the benzene rings of the compounds.

CN patent 200710034357 discloses some similar compounds having the above structures with anti-fibrosis activity and a compound with the anti-fibrosis activity shown in the structural formula IV.

Structural formula IV

Those compounds are provided with TFM at the 5-position of the pyridone ring without any substitutents on the aromatic ring of the phenyl group, thereby overcoming the disadvantages of inferior action of Pirfenidone.

DE patent DE4343528 reports a class of compounds having insecticidal actions for agricultural use, with the structural formula V as follows.

Structural formula V

In structural formula V, A and B are substituted by various heterocyclic rings, such as furan, imidazole, pyridine and pyridone; wherein a class of compounds with the structural formula VI is included.

Structural formula VI

EP patents EP259048, EP367410 and EP398499 report a class of compounds having insecticidal actions for use in agriculture, with the structural formula VII as follows:

Structural formula VII wherein a class of compounds having the structural formula VIII, in which $R_1$ is pyridone and $R_{10}$ is O or S, is included.

Structural formula VIII

EP patent EP216541 reports a class of compounds having insecticidal actions for use in agriculture, with the structural formula IX as follows:

Structural formula IX wherein a class of compounds with the structural formula X is included.

Structural formula X

EP patent EP488220 reports a class of compounds having insecticidal actions, with the structural formula XI as follows:

Structural formula XI

In structures of the above-mentioned compounds, the pyridine ring and the benzene ring at the 1-position of the pyridine ring have a plurality of substituents; the compounds with complicated structures have not been reported to have the anti-fibrosis function. In the meanwhile, more fluorine atoms in the structure will result in stronger lipid solubility of the molecule.

DE102004027359 discloses a class of compounds capable of modulating dopamine-3 receptor activity and applied to treatment of Parkinson's disease and schizophrenosis;

Structural formula XII wherein, A is a hydrocarbon chain with 4-6 atoms, having 1-2 substituted methyl groups thereon; or 1-2 carbon atoms in the carbon chain are substituted by O, C=O, S and other atoms; R1 and R2 are H, CN, NO2, a halogen atom, $OR^5$, $NR^6R^7$, $C(O)_NR^6R^7$, $O-C(O)_NR^6R^7$; C1-C6 alkyl, C1-C6 haloalkyl, etc.

SUMMARY OF THE INVENTION

The invention provides 1-(substituted benzyl)-5-trifluoromethyl-2-(1H)pyridine compounds shown in structural formula XIII, Structural formula XIII wherein R1-R4, R12 are selected from H, CN, $NO_2$, hydroxyl, amino, a halogen atom, $C_1$-$C_6$ alkoxyl, $NR^{10}R^{11}$, $OR^{13}$, $C(O)R^{14}$, $O-C(O)R^{14}R^{15}$, $C_1$-$C_6$ alkyl, $C_1$-$C_6$ haloalkyl, $C^2$-$C^6$ alkenyl, carboxyl and carboxylic ester; wherein R1-R4 and R12 are not simultaneously H, $R^{14}$ and $R^{15}$ are selected from $C_1$-$C_6$ alkyl; where in $NR^{10}R^{11}$, $R^{10}$ and $R^{11}$ are selected from H, $C_1$-$C_6$ hydroxyalkyl, esterified $C_1$-$C_6$ hydroxyalkyl, $C_1$-$C_6$ alkoxyalkyl, or structural formula XIV, and $R^{10}$ and $R^{11}$ are not simultaneously H; and in $OR^{13}$, $R^{13}$ is selected from hydroxyalkyl or alkoxyalkyl.

Structural formula XIV wherein, in structural formula XIV, R5 is selected from H, $C_1$-$C_6$ alkyl, $C_1$-$C_6$ haloalkyl, $C_1$-$C_6$ hydroxyallyl, and $C_2$-$C_6$ alkenyl; R6-R9 are selected from H, $C_1$-$C_6$ alkoxyl, =O, $C_1$-$C_4$ alkyl, $C_1$-$C_4$ haloalkyl, $C_1$-$C_4$ hydroxyalkyl, and $C_2$-$C_4$ alkenyl; X is selected from N and CH; Y is selected from N, O, and C, with the proviso that, when Y is O, R5 is absent; and n is 1-6;

and pharmaceutically available salts, including hydrochlorate, sulfate, phosphate, perchlorate, methanesulfonate, trifluoromethanesulfonate, formate, acetate, propionate, butyrate, maleate, succinate, trifluoroacetate, succinate, salicylate, DL-aspartate, D-aspartate, L-aspartate, DL-glutamate, D-glutamate, L-glutamate, glycerate, succinate, stearate, DL-tartrate, D-tartrate, L-tartrate, (+/−)-mandelate, (R)-(−)-mandelate, (S)-(+)-mandelate, citrate, mucate, maleate, malonate, benzoate, DL-malate, D-malate, L-malate, hemimalate, 1-adamantane acetate, 1-adamantane carboxylate, flavianate, sulfoacetate, (+/−)-lactate, L-(+)-lactate, D-(−)-lactate, pamoate, D-α-galacturonic acid salt, glycerate, DL-cystine salt, D-cystine salt, L-cystine salt, DL-homocystine salt, D-homocystine salt, L-homocystine salt, DL-cysteine salt, D-cysteine salt, L-cysteine salt, (4S)-hydroxy-L-proline, cyclopropane-1,1-dicarboxylate, 2,2-methyl malonate, tyrosine salt, proline salt, fumarate, 1-hydroxy-2-naphthoate, phosphonoacetate, carbonate, bicarbonate, 3-phosphonopropionate, DL-pyroglutamate, D-pyroglutamate, L-pyroglutamate, toluenesulfonate, benzenesulfonate, esilate, (+/−)-camsilate, naphthalenesulfenesulfonate, 1R-(−)-camsilate, 1S-(+)-camsilate, 1,5-napadisilate, 1,2-ethanedisulphonate, 1,3-propanedisulphonate, 3-(N-morpholino) propane sulphonate, biphenyl sulphonate, isethionate, 1-hydroxy-2-naphthalenesulfenesulfonate, dihydric phosphate, potassium hydrogen phosphate, dipotassium phosphate, potassium phosphate, sodium hydrogen phosphate, disodium phosphate, sodium phosphate, sodium dihydrogen phosphate, calcium phosphate, tertiary calcium phosphate, hexafluoro phosphate, ethenyl phosphate, 2-carboxylethyl phosphate and phenyl phosphate.

More preferably, one of R1-R4 and R12 is $NR^{10}R^{11}$ or $OR^{13}$.

According to embodiments of the invention, more preferably, others are H if one of R1-R4 and R12 is $NR^{10}R^{11}$ or $OR^{13}$.

According to embodiments of the invention, the following compounds are preferred:
1-(4-nitrobenzyl)-5-(trifluoromethyl)pyridin-2(1H)-one;
1-(4-amino-benzyl)-5-(trifluoromethyl)pyridin-2(1H)-one;
1-(4-((3-morpholinylpropyl)amino)benzyl)-5-(trifluoromethyl)pyridin-2(1H)-one;
1-(4-(((3-piperidin-1-yl)propyl)amino)benzyl)-5-(trifluoromethyl)pyridin-2(1H)-one;
1-(4-((3-(4-methyl-piperazin-1-yl)propyl)amino)benzyl)-5-(trifluoromethyl)pyridin-2(1H)-one;
1-(4-((2-hydroxyethyl)amino)benzyl)-5-(trifluoromethyl)pyridin-2(1H)-one;
1-(4-((2-(piperidyl-1-yl)ethyl)amino)benzyl)-5-(trifluoromethyl)pyridin-2(1H)-one;
1-(4-((2-morpholinylethyl)amino)benzyl)-5-(trifluoromethyl)pyridin-2(1H)-one;
1-(4-((2-(4-methyl-piperazin-1-yl)ethyl)amino)benzyl)-5-(trifluoromethyl)pyridin-2(1H)-one;
1-(4-((2-(piperazin-1-yl)ethyl)amino)benzyl)-5-(trifluoromethyl)pyridin-2(1H)-one;
1-(4-((2-(4-(2-hydroxyethyl)piperazin-1-yl)ethyl)amino)benzyl)-5-(trifluoromethyl)pyridin-2(1H)-one;
1-(4-((2-(4-methyl-piperazin-1-yl) ethyl)amino)benzyl)-5-(trifluoromethyl)pyridin-2(1H)-one dihydrochloride;
1-(4-acetamide-benzyl)-5-(trifluoromethyl)pyridin-2(1H)-one;
1-(2,6-dichlorobenzyl)-5-(trifluoromethyl)pyridin-2(1H)-one;
1-(4-fluorobenzyl)-5-(trifluoromethyl)pyridin-2(1H)-one;
1-(2-nitrobenzyl)-5-(trifluoromethyl)pyridin-2(1H)-one;
1-(2-amino benzyl)-5-(trifluoromethyl)pyridin-2(1H)-one;
1-(3-chlorobenzyl)-5-(trifluoromethyl)pyridin-2(1H)-one;
1-(4-methoxybenzyl)-5-(trifluoromethyl)pyridin-2(1H)-one;
1-(2-fluorobenzyl)-5-(trifluoromethyl)pyridin-2(1H)-one;
1-(2-(2-hydroxyethylamino)benzyl-5-(trifluoromethyl)pyridin-2(1H)-one;
1-(2-(2-(piperazin-1-yl)ethylamino)benzyl)-5-(trifluoromethyl)pyridin-2(1H)-one;
1-(2-(2-(4-methylpiperazin-1-yl)ethylamino)benzyl)-5-(trifluoromethyl)pyridin-2(1H)-one;
1-(2-acetamide-benzyl)-5-(trifluoromethyl)pyridin-2(1H)-one;
1-(2-(2-morpholinoethylamino)benzyl)-5-(trifluoromethyl)pyridin-2(1H)-one;
1-(4-(2-(2-hydroxyethoxy)ethylamino)benzyl)-5-(trifluoromethyl)pyridin-2(1H)-one;

The invention also provides a synthetic method for compounds listed above, including: reacting 5-trifluoromethyl-2(1H)pyridone with substituted benzyl bromide, with DMSO as solvent, and potassium carbonate as an acid-binding agent to prepare a simple phenyl-substituted compound, shown in reaction formula I. The synthetic starting product trifluoromethyl pyridone is a commercial material.

Reaction formula I

To prepare a simple amino-substituted compound, following reaction formula I to form nitro substituted derivatives; the nitro substituent is reduced by iron powder in the presence of hydrochloric acid and target products are prepared according to different compounds, shown in reaction formula II.

Reaction formula II

-continued

A compound, in which an amino group is bonded to a heterocyclic ring through an aliphatic side chain, is prepared including the steps of: preparing an amino-substituted compound; and then reacting with a heterocyclic compound with haloalkyl side chains, with DMF as solvent, potassium carbonate as an acid-binding agent and sodium iodide as a catalyst, as shown in the reaction formula III.

Reaction formula III or the target product is prepared by reacting an hydroxyethyl amino substituted compound prepared according to reaction formula II with thionyl chloride to produce a chloroethyl amino substituted compound, and then reacting with the heterocyclic compound, as shown in reaction formula IV.

Reaction formula IV

The above-mentioned compound is used for preparing a broad-spectrum medicament for fibrosis.

In the invention, based on the prior art, a substituted amino group is introduced onto the benzene ring at 1-position of pyridone; a hydrophilic group such as hydroxyl group and heterocyclic ring is introduced onto the amino group through an alkyl chain, thus obtaining a class of new pyridone compounds and salts thereof. The activity of the compounds is greatly enhanced.

The applicant finds that the produced compounds have relatively higher effects than the conventional pyridone compound by modifying the phenyl group by the substituted amino group on the basis of 1-phenyl-5-trifluoromethyl-pyridone; simultaneously the compounds including heterocyclic rings could be produced into various salts which are beneficial to being prepared into various liquid formulations.

DETAILED DESCRIPTION OF PREFERRED EMBODIMENTS

Example 1

Figure 1:
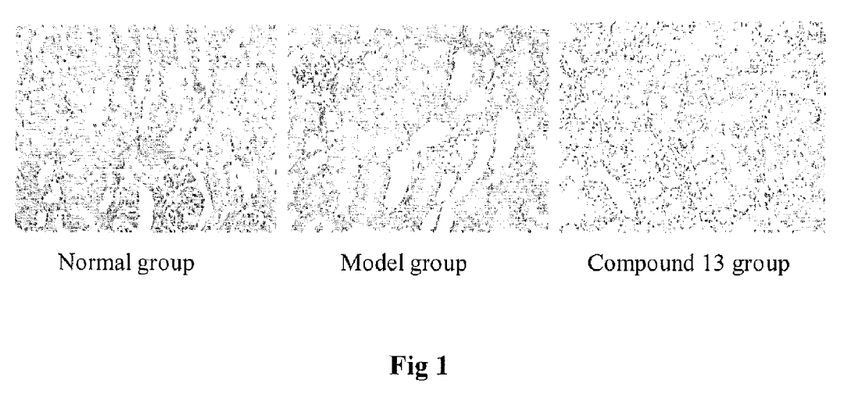
FIG. 1 HE staining for renal pathology in embodiment 28 (×200)
Figure 2:
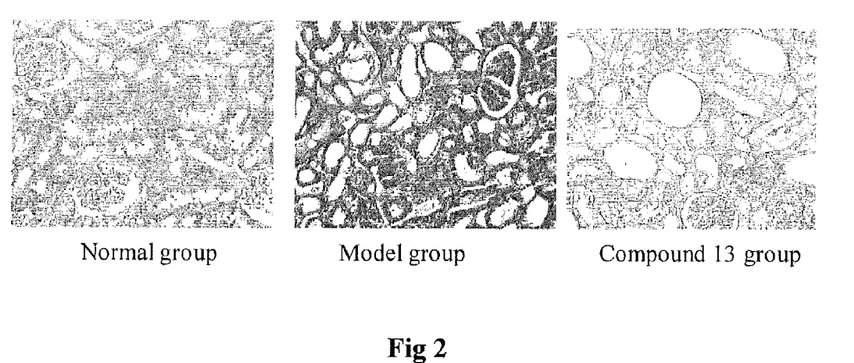
FIG. 2 Masson staining for renal pathology in embodiment 28 (×200)

Preparation of 1-(4-nitrobenzyl)-5-(trifluoromethyl) pyridin-2(1H)-one (Compound 1)

The preparation of 1-(4-nitrobenzyl)-5-(trifluoromethyl)pyridin-2(1H)-one includes steps of: adding 8.2 g (0.050 mol) of 5-(trifluoromethyl)pyridin-2(1H)-one in 100 ml of DMSO for dissolving; adding 16.2 g (0.075 mol) of 1-(bromomethyl)-4-nitrobenzene, 11.0 g (0.080 mol) of potassium carbonate and allowing the resulting system to react at 85° C. for 4 hours under stirring; after reaction, cooling to 40° C.; adding 100 ml of 12% ammonia solution; separating out a great amount of precipitate; filtering; dissolving the filter residue with ethyl acetate; decolorizing by active carbon; filtering; drying the filtrate by anhydrous sodium sulfate overnight; filtering out sodium sulfate; reclaiming part of solvent to form crystals; filtering to obtain the product of 1-(4-nitrobenzyl)-5-(trifluoromethyl)pyridin-2(1H)-one. The product is 11.4 g of brown solid. m.p.: 121~123° C.; EI-MS (m/z): 288[M]$^+$; $^1$H-NMR (CDCl$_3$, 300 MHz) δ ppm: 5.240 (s, 2H, —CH$_2$—), 6.694~6.726 (d, 1H, J=9.6 Hz, Ar—H), 7.466~7.482 (d, 2H, J=4.8 Hz, Ar—H), 7.495 (s, 1H, Ar—H), 7.514~7.522 (d, 1H, J=2.4 Hz, Ar—H), 7.705 (s, 1H, Ar—H), 8.222~8.251 (d, 1H, J=8.7 Hz, Ar—H).

Example 2

Preparation of 1-(4-amino-benzyl)-5-(trifluoromethyl)pyridin-2(1H)-one (Compound 2)

The preparation of 1-(4-amino-benzyl)-5-(trifluoromethyl)pyridin-2(1H)-one includes step of: heating 11.4 g (0.037 mol) of 1-(4-nitrobenzyl)-5-(trifluoromethyl)pyridin-2(1H)-one, 200 mL of 50% ethanol and 6.28 g (0.112 mol) of reductive iron powder to reflux; slowly adding dropwise 0.42 mL (0.004 mol) of concentrated HCl (dropping after dilution by 5 mL of 50% ethanol); refluxing for 4 hours under stirring; after reaction, regulating pH value to 10 by 15% KOH ethanol solution; filtering; washing the filter residues with 95% ethanol (2×10 mL); extracting with ethyl acetate (50 mL×3) after evaporating ethanol from the filtrate; drying the organic phase with anhydrous sodium sulfate overnight; filtering; and evaporating filtrate to obtain the product of 1-(4-amino-benzyl)-5-(trifluoromethyl)pyridin-2(1H)-one. The product is 9.9 g of brown solid powders. m.p. 97~98° C. ESI-MS (m/z): 291[M+Na]$^+$ 1H-NMR (CDCl$_3$, 300 MHz) δ ppm: 4.255 (br, 2H, —NH2), 5.023 (s, 2H, —CH$_2$—), 6.629~6.661 (d, 1H, J=59.6 Hz, Ar—H), 6.713~6.740 (d, 2H, J=8.1 Hz, Ar—H), 7.137~7.164 (d, 2H, J=8.1 Hz, Ar—H), 7.393~7.433 (dd, 1H, J=2.4 Hz, 9.6 Hz, Ar—H), 7.627 (s, 1H, Ar—H).

Example 3

Preparation of 1-(4-((3-morpholinylpropyl)amino) benzyl)-5-(trifluoromethyl)pyridin-2(1H)-one (Compound 3)

The preparation of 1-(4-((3-morpholinylpropyl)amino) benzyl)-5-(trifluoromethyl)pyridin-2(1H)-one includes steps of adding 20 mL of N,N-dimethylformamide to dissolve 2.01 g (0.0075 mol) of 1-(4-amino-benzyl)-5-(trifluoromethyl)pyridin-2(1H)-one; adding 0.69 g (0.005 mol) of potassium carbonate, 0.42 g (0.0025 mol) of 1-(3-chloro)propyl-morpholine and a catalytic amount of sodium iodide and allowing the resulting system to react at 130° C. for 48 hours under stirring; filtering, evaporating filtrate to dryness; and separating residues by chromatography with eluent of petroleum ether and ethyl acetate with proportion of 1:1 (2% triethylamine) to obtain 0.5 g of yellow oil. ESI-MS (m/z): 396 [M+H]$^+$; $^1$H-NMR (CDCl$_3$, 300 MHz) δ ppm: 1.662~1.750 (m, 2H, —CH$_2$—), 2.398~2.569 (m, 6H, —CH$_2$—), 3.103~3.143 (t, 2H, —CH$_2$—), 3.665~3.756 (t, 4H, —CH$_2$—), 4.780 (br, 1H, —NH—), 4.934 (s, 2H, —CH$_2$—), 6.438~0.607 (m, 3H, Ar—H), 7.065~7.092 (2H, Ar—H), 7.314~7.373 (1H, Ar—H), 7.553 (s, 1H, Ar—H).

Example 4

Preparation of 1-(4-(((3-piperidin-1-yl)propyl)amino)benzyl)-5-(trifluoromethyl)pyridin-2(1H)-one (Compound 4)

The preparation of 1-(4-(((3-piperidin-1-yl)propyl)amino)benzyl)-5-(trifluoromethyl)pyridin-2(1H)-one includes steps of: adding 12 mL of acetonitrile to dissolve 1.28 g (0.0048 mol) of 1-(4-amino-benzyl)-5-(trifluoromethyl)pyridin-2(1H)-one; adding 1.10 g (0.008 mol) of potassium carbonate, 0.64 g (0.004 mol) of 1-(3-chloro)propylpiperidine and a catalytic amount of sodium iodide and heating the resulting system to reflux for 48 hours under stirring; filtering, evaporating filtrate to dryness; and separating residues by chromatography with eluent of petroleum ether and ethyl acetate with proportion of 1:2 (1% triethylamine) to obtain 0.22 g of off-white solid. m.p.: 168~170° C. ESI-MS (m/z): 394[+H]$^+$. $^1$H-NMR (CDCl$_3$, 300 MHz) δ ppm: 1.582 (br, 2H, —CH$_2$—), 1.859~1.875 (m, 4H, —CH$_2$—), 2.009~2.071 (m, 4H, —CH$_2$—) 2.806~2.851 (t, 6H, —CH$_2$—), 3.247~3.286 (t, 2H, —CH$_2$—), 4.252 (br, 1H, —NH—), 5.002 (s, 2H, —CH$_2$—), 6.581~6.609 (d, 2H, J=8.4 Hz, Ar—H), 6.620~6.653 (d, 1H, J=9.9 Hz, Ar—H), 7.126~7.154 (d, 2H, J=8.4 Hz, Ar—H), 7.385~7.424 (dd, 1H, J=2.1 Hz, 9.6 Hz, Ar—H), 7.553 (s, 1H, Ar—H).

Example 5

Preparation of 1-(4-((3-(4-methyl-piperazin-1-yl)propyl)amino)benzyl)-5-(trifluoromethyl)pyridin-2(1H)-one (Compound 5)

The preparation of 1-(4-((3-(4-methyl-piperazin-1-yl)propyl)amino)benzyl)-5-(trifluoromethyl)pyridin-2(1H)-one includes steps of adding 3 mL of ethanol to dissolve 0.402 g (0.0015 mol) of 1-(4-amino-benzyl)-5-(trifluoromethyl)pyridin-2(1H)-one; adding 0.088 g (0.0005 mol) of 1-(3-chloropropyl)-4-methylpiperazine and feeding a catalytic amount of potassium iodide; carrying out microwave reaction at 110° C.; after reaction, filtering; evaporating filtrate to dryness; and separating residue by column chromatography with eluent of petroleum ether and ethyl acetate with proportion of 1:2 (1% triethylamine) to obtain 0.13 g of yellow oil. ESI-MS (m/z): 409 [M+H]$^+$. $^1$H-NMR (CDCl$_3$, 300 MHz) δ ppm: 1.696~1.802 (m, 2H, —CH$_2$—), 2.264 (s, 3H, —CH$_3$), 2.427~2.470 (m, 10H—CH$_2$—), 3.094~3.136 (t, 2H, —CH$_2$—), 4.936 (s, 2H—CH$_2$—), 6.488~6.516 (d, 2H, J=8.4 Hz, Ar—H), 6.552~6.583 (d, 1H, J=9.3 Hz, Ar—H), 7.061~7.091 (d, 2H, J=9.0 Hz, Ar—H), 7.312~7.352 (dd, 1H, J=2.4 Hz, 9.6 Hz, Ar—H), 7.551 (s, 1H, Ar—H).

Example 6

Preparation of 1-(4-((2-hydroxyethyl)amino)benzyl)-5-(trifluoromethyl)pyridin-2(1H)-one (Compound 6)

The preparation of 1-(4-((2-hydroxyethyl)amino)benzyl)-5-(trifluoromethyl)pyridin-2(1H)-one includes steps of: adding 100 mL of n-butanol to dissolve 8.4 g (0.03 mol) of 1-(4-amino-benzyl)-5-(trifluoromethyl)pyridin-2(1H)-one; adding 4.1 g (0.03 mol) of potassium carbonate and 5.6 g (0.06 mol) of chloroethanol and allowing the resulting system to react at 130° C. for 12 hours under stirring; filtering; evaporating filtrate to dryness; and separating residue by column chromatography with eluent of petroleum ether and ethyl acetate with proportion of 1:1 to obtain 2.0 g of off-white solid. m.p.: 97=98° C. ESI-MS (m/z): 335 [M+Na]$^+$.
$^1$H-NMR (CDCl$_3$, 300 MHz) δ ppm: 3.293~3.28 (t, 2H, —CH$_2$—), 3.829~3.864 (t, 2H, —CH$_2$—), 5.015 (s, 2H, —CH$_2$—), 6.623~6.652 (d, 2H, J=8.7 Hz, Ar—H), 7.151~7.179 (d, 2H, J=8.4 Hz, Ar—H), 7.383~7.424 (dd, 1H, J=2.7 Hz, 9.6 Hz, Ar—H), 7.446~7.4588 (dd, 1H, J=2.7 Hz, 8.1 Hz, Ar—H), 7.621 (s, 1H, Ar—H).

Example 7

Preparation of 1-(4-((2-(piperidyl-1-yl)ethyl)amino)benzyl)-5-(trifluoromethyl)pyridin-2(1H)-one (Compound 7)

A. Preparation of 1-(4-((2-chloroethyl)amino)benzyl)-5-(trifluoromethyl)pyridin-2(1H)-one The preparation of 1-(4-((2-chloroethyl)amino)benzyl)-5-(trifluoromethyl)pyridin-2(1H)-one includes steps of: dissolving 2.9 mmol of 1-(4-((2-hydroxyethyl)amino)benzyl)-5-(trifluoromethyl)pyridin-2(1H)-one by 30 ml of dichloromethane; adding 0.22 ml of sulfurous dichloride and 0.44 ml of triethylamine; allowing the resulting system to react at room temperature for 12 h under stirring; and separating residue by column chromatography with eluent of petroleum ether and ethyl acetate with proportion of 3:1 to obtain 0.24 g of white solid.

EI-MS (m/z):330[M]$^+$. $^1$H-NMR (CDCl$_3$, 300 MHz) δ ppm: 3.485~3.525 (t, 2H, —CH$_2$—), 3.689~3.728 (t, 2H, —CH$_2$—), 4.181 (br, 1H, —NH—), 5.020 (s, 2H, —CH$_2$—), 6.612~6.656 (m, 3H, Ar—H), 7.167~7.195 (d, 2H, J=8.4 Hz, Ar—H), 7.385~7.426 (dd, 1H, J=2.7 Hz, 9.6 Hz, Ar—H), 7.623 (s, 1H, Ar—H).

B. Preparation of 1-(4-((2-(piperidyl-1-yl)ethyl)amino)benzyl)-5-(trifluoromethyl) pyridin-2(1H)-one The preparation of 1-(4-((2-(piperidyl-1-yl)ethyl)amino)benzyl)-5-(trifluoromethyl)pyridin-2(1H)-one includes steps of: dissolving 0.24 g (0.7 mmol) of 1-(4-((2-chloroethyl)amino)benzyl)-5-(trifluoromethyl)pyridin-2(1H)-one in 30 mL of acetonitrile; adding 0.37 g (4.2 mmol) of piperidine; carrying out refluxing reaction for 27 hours; filtering; evaporating filtrate to dryness; and separating by column chromatography with eluent of ethyl acetate and methanol with proportion of 10:1 to obtain 0.27 g of yellow solid. m.p.: 83.6~85.5° C. EI-MS (m/z): 379[M]$^+$. $^1$H-NMR (CDCl$_3$, 300 MHz) δ ppm: 1.672 (s, 2H, —CH$_2$—), 1.872 (s, 4H, —CH$_2$—), 2.817~3.112 (br, 6H, —CH$_2$—), 3.542 (s, 2H, —CH$_2$—), 5.012 (s, 2H, —CH$_2$—), 5.174 (br, 1H, —NH—), 6.618~6.649 (d, 1H, J=9.3 Hz, Ar—H), 6.698~6.726 (d, 2H, J=8.4 Hz, Ar—H), 7.152~7.181 (d, 1H, J=8.7 Hz, Ar—H), 7.386~7.427 (dd, 1H, J=2.7 Hz, 9.6 Hz, Ar—H), 7.627 (s, 1H, Ar—H).

Example 8

Preparation of 1-(4-((2-morpholinylethyl)amino)benzyl)-5-(trifluoromethyl)pyridin-2(1H)-one (Compound 8)

The preparation of 1-(4-((2-morpholinylethyl)amino)benzyl)-5-(trifluoromethyl)pyridin-2(1H)-one includes steps of: dissolving 0.26 g (0.79 mmol) of 1-(4-((2-chloroethyl)amino)benzyl)-5-(trifluoromethyl)pyridin-2(1H)-one in 30 mL of acetonitrile; adding 0.41 g (4.7 mmol) of morpholine; carrying out refluxing reaction for 46 hours; filtering; evaporating filtrate to dryness; and separating by column chromatography with eluent of ethyl acetate and methanol with proportion of 10:1 to obtain 0.29 g of brown oil.

EI-MS (m/z): 381[M]$^+$. $^1$H-NMR (CDCl$_3$, 300 MHz) δ ppm: 2.471~2.484 (br, 4H, —CH$_2$—), 2.614~2.653 (t, 2H, —CH$_2$—), 3.142~3.181 (t, 2H, —CH$_2$—), 3.704~3.735 (t, 4H, —CH$_2$—), 4.439 (br, 1H, —NH—), 5.012 (s, 2H, —CH$_2$—), 6.597~6.650 (m, 3H, Ar—H), 7.150~7.178 (d, 2H, Ar—H), 7.137~7.417 (dd, 1H, J=2.7 Hz, 9.6 Hz, Ar—H), 7.620 (s, 1H, Ar—H).

Example 9

Preparation of 1-(4-((2-(4-methyl-piperazin-1-yl)ethyl)amino)benzyl)-5-(trifluoromethyl)pyridin-2(1H)-one (Compound 9)

The preparation of 1-(4-((2-(4-methyl-piperazin-1-yl)ethyl)amino)benzyl)-5-(trifluoromethyl)pyridin-2(1H)-one includes steps of: dissolving 0.33 g (1.0 mmol) of 1-(4-((2-chloroethyl)amino)benzyl)-5-(trifluoromethyl)pyridin-2(1H)-one in 30 mL of acetonitrile; adding 0.60 g (6.0 mmol) of N-methylpiperazine; carrying out refluxing reaction for 38 hours; filtering; evaporating filtrate to dryness; and separating by column chromatography with eluent of ethyl acetate and methanol with proportion of 10:1 to obtain 0.31 g of brown oil. EI-MS (m/z): 394[M]$^+$. $^1$H-NMR (CDCl$_3$, 300 MHz) δ ppm: 2.314 (s, 3H, —CH$_3$), 2.512 (br, 8H, —CH$_2$—), 2.622~2.661 (t, 2H, —CH$_2$—), 3.152 (s, 2H, —CH$_2$—), 4.436 (br, 1H, —NH—), 5.011 (s, 2H, —CH$_2$—), 6.592~6.650 (t, 3H, Ar—H), 7.147~7.175 (d, 2H, Ar—H), 7.377~7.417 (dd, 1H, J=2.4 Hz, 9, 6 Hz, Ar—H), 7.622 (s, 1H, Ar—H).

Example 10

Preparation of 1-(4-((2-(piperazin-1-yl)ethyl)amino)benzyl)-5-(trifluoromethyl)pyridin-2(1H)-one (Compound 10)

The preparation of 1-(4-((2-(piperazin-1-yl)ethyl)amino)benzyl)-5-(trifluoromethyl)pyridin-2(1H)-one includes steps of: dissolving 0.39 g (1.2 mmol) of 1-(4-((2-chloroethyl)amino)benzyl)-5-(trifluoromethyl)pyridin-2(1H)-one in 30 mL of acetonitrile; adding 0.82 g (9.6 mmol) of piperazine; carrying out refluxing reaction for 18 hours; filtering; evaporating filtrate to dryness; and separating by column chromatography with eluent of ethyl acetate and methanol with proportion of 1:1 to obtain 0.37 g of colorless oil. EI-MS (m/z): 380 [M]⁺. ¹H-NMR (CDCl₃, 300 MHz) δ ppm: 2.445 (br, 4H, —CH₂—), 2.593~2.632 (t, 2H, —CH₂—), 2.855~2.915 (t, 4H, —CH₂—), 3.132~3.170 (t, 2H, —CH₂—), 4.438 (br, 1H, —NH—), 5.011 (s, 2H, —CH₂—), 6.595~6.650 (t, 3H, Ar—H), 7.147~7.175 (d, 2H, Ar—H), 7.377~7.417 (dd, 1H, J=2.4 Hz, 9.6 Hz, Ar—H), 7.625 (s, 1H, Ar—H).

Example 11

Preparation of 1-(4-((2-(4-(2-hydroxyethyl)piperazin-1-yl)ethyl)amino)benzyl)-5-(trifluoromethyl)pyridin-2(1H)-one (Compound 11)

The preparation of 1-(4-((2-(4-(2-hydroxyethyl)piperazin-1-yl)ethyl)amino)benzyl)-5-(trifluoromethyl)pyridin-2(1H)-one includes steps of: dissolving 0.83 g (2.5 mmol) of 1-(4-((2-chloroethyl)amino)benzyl)-5-(trifluoromethyl)pyridin-2(1H)-one and 2.6 g (20 mmol) of hydroxyethyl piperazine in 30 mL of acetonitrile; adding an amount of sodium iodide; carrying out refluxing reaction for 29 hours; filtering; evaporating filtrate to dryness; and separating by column chromatography with eluent of petroleum ether and ethyl acetate with proportion of 10:1 to obtain 0.60 g of yellow oil. EI-MS (m/z): 424[M]⁺. ¹H-NMR (CDCl₃, 300 MHz) δ ppm: 2.572~2.268 (m, 12H, —CH₂—), 3.151~3.150 (t, 2H, —CH₂—), 3.638~3.673 (t, 2H, —CH₂—), 5.011 (s, 2H, —CH₂—), 6.593~6.649 (t, 3H, Ar—H), 7.148~7.176 (d, 2H, J=8.4 Hz, Ar—H), 7.37 7~7.418 (dd, 1H, J=2.7 Hz, 9.6 Hz, Ar—H), 7.620 (s, 1H, Ar—H).

Example 12

Preparation of 1-(4-((2-(4-methyl-piperazin-1-yl)ethyl)amino)benzyl)-5-(trifluoromethyl)pyridin-2(1H)-one dihydrochloride (Compound 12)

The preparation of 1-(4-((2-(4-methyl-piperazin-1-yl)ethyl)amino)benzyl)-5-(trifluoromethyl)pyridin-2(1H)-one dihydrochloride includes steps of: dissolving 0.12 g (1.1 mmol) of 1-(4-((2-(4-methyl-piperazin-1-yl)ethyl)amino)benzyl)-5-(trifluoromethyl)pyridin-2(1H)-one by 20 ml of ethanol; adding 0.075 mL of hydrochloric acid; mixing for reaction for 40 m in under stirring; evaporating solvent to dryness to obtain 1-(2-chloro-4-(((3-piperidin-1-yl)propyl)amino)phenyl)-5-(trifluoromethyl)pyridin-2(1H)-one dihydrochloride which is yellow solid of 0.09 g. EI-MS (m/z): 394[M]⁺. ¹H-NMR (D₂O) δ ppm: 2.961 (s, 3H, —CH₃), 3.182~3.236 (t, 2H, —CH₂—), 3.299 (s, 2H, —H), 3.389~3.438 (t, 2H, —CH₂—), 3.565 (br, 8H, —CH═), 5.216 (s, 2H, —CH₂—), 6.700~6.731 (d, 1H, Ar—H), 7.229~7.257 (d, 2H, J=8.4 Hz, Ar—H), 7.340~7.368 (d, 2H, J=8.4 Hz, Ar—H), 7.792~7.823 (d, 1H, J=9.3 Hz, Ar—H), 8.275 (s, 1H, Ar—H).

Example 13

Preparation of 1-(4-acetamide-benzyl)-5-(trifluoromethyl)pyridin-2(1H)-one (Compound 13)

The preparation of 1-(4-acetamide-benzyl)-5-(trifluoromethyl)pyridin-2(1H)-one includes steps of: dissolving 1.1 mol of acetic anhydride and 0.268 g (1 mmol) of 1-(4-amino-benzyl)-5-(trifluoromethyl)pyridin-2(1H)-one in 20 ml of acetic acid; carrying out refluxing reaction for 2 hours; adding 20 ml of water and extracting by ethyl ether (2*20 mL); washing the organic phase with 15% sodium bicarbonate solution and drying the organic phase by anhydrous sodium sulfate; filtering; and evaporating filtrate; and separating residue by column chromatography with eluent of chloroform and methanol with proportion of 50:1 to obtain 0.20 g of white solid. m.p.: 225.3~227.2° C. ESI-MS (m/z): 333 [+Na]⁺. ¹H-NMR (DMSO) δ ppm: 3.513 (s, 3H, —CH₃), 5.098 (s, 2H, —CH₂—), 6.566~6.598 (d, 1H, J=9, 6 Hz, Ar—H), 7.269~7.296 (d, 2H, J=8.1 Hz, Ar—H), 7.524~7.551 (d, 2H, J=8.1 Hz, Ar—H), 7.678~7.704 (d, 1H, J=8.4 Hz, Ar—H), 8.5124 (s, 1H, Ar—H), 10.009 (s, 1H, —NH).

Example 14

Preparation of 1-(2,6-dichlorobenzyl)-5-(trifluoromethyl)pyridin-2(1H)-one

(Compound 14)

The preparation of 1-(2,6-dichlorobenzyl)-5-(trifluoromethyl)pyridin-2(1H)-one includes steps of: dissolving 0.49 g (3.0 mmol) of 5-(trifluoromethyl)pyridin-2(1H)-one in 30 ml of DMF; adding 0.5 g (3.6 mmol) of sodium carbonate and 0.88 g (4.5 mmol) 1,3-dichloro-2-(chloromethyl)benzene; carrying out refluxing reaction for 3 hours; filtering; evaporating filtrate; and separating residue by column chromatography with eluent of petroleum ether to obtain 0.72 g of the product 1-(2,6-dichlorobenzyl)-5-(trifluoromethyl)pyridin-2(1H)-one as a light-yellow solid. m.p.: 74.0~76.0° C. EI-MS (m/z): 321 [M−1]$^+$. $^1$H-NMR (CDCl$_3$, 300 MHz) δ ppm: 5.442 (s, 2H, —CH$_2$—), 6.665~6.697 (d, 1H, J=9.6 Hz, Ar—H), 7.266 (1H, Ar—H), 7.318~7.431 (dd, 1H, J=7.2 Hz, 9.3 Hz, Ar—H), 7.413~7.460 (m, 3H, Ar—H).

Example 15

Preparation of 1-(4-fluorobenzyl)-5-(trifluoromethyl)pyridin-2(1H)-one (Compound 15)

The preparation of 1-(4-fluorobenzyl)-5-(trifluoromethyl)pyridin-2(1H)-one includes steps of: dissolving 0.49 g (3.0 mmol) of 5-(trifluoromethyl)pyridin-2(1H)-one in 30 ml of DMF; adding 0.5 g (3.6 mmol) of sodium carbonate and 0.85 g (4.5 mmol) 1-(bromomethyl)-4-fluorobenzene; carrying out refluxing reaction for 3 hours; filtering; evaporating filtrate; and separating residue by column chromatography with eluent of petroleum ether to obtain 0.72 g of the product 1-(4-fluorobenzyl)-5-(trifluoromethyl)pyridin-2(1H)-one as a white solid. m.p.: 70.1~72.0° C. ESI-MS (m/z): 294[M+Na]$^+$. $^1$H-NMR (CDCl$_3$, 300 MHz) δ ppm: 5.112 (s, 2H, —CH$_2$—), 6.658~6.690 (d, 1H, J=9.6 Hz, Ar—H), 7.035~7.093 (m, 2H, Ar—H), 7.299~7.345 (m, 2H, Ar—H), 7.4123~7.464 (dd, 1H, J=2.7 Hz, 9.6 Hz, Ar—H), 7.649 (s, 1H, Ar—H).

Example 16

Preparation of 1-(2-nitrobenzyl)-5-(trifluoromethyl)pyridin-2(1H)-one (Compound 16)

The preparation of 1-(2-nitrobenzyl)-5-(trifluoromethyl)pyridin-2(1H)-one includes steps of: dissolving 12.3 g (0.075 mol) of 5-(trifluoromethyl)pyridin-2(1H)-one in 200 ml of DMF; adding 16.6 g (0.12 mol) of sodium carbonate and 24.5 g (0.113 mol) 1-(bromomethyl)-2-nitrobenzene; carrying out refluxing reaction for 4 hours; cooling to 40° C.; adding 40 ml of 15% ammonia solution; extracting by ethyl acetate (50 mL×3); decolorizing by active carbon; drying by anhydrous sodium sulfate; filtering; evaporating filtrate; and separating residue by column chromatography to obtain the 12.2 g of the product 1-(2-nitrobenzyl)-5-(trifluoromethyl)pyridin-2(1H)-one as a white solid. m.p.: 100.0102.0° C. EI-MS (m/z): 298[M]$^+$. $^1$H-NMR (CDCl$_3$, 300 MHz) δ ppm: 5.547 (s, 2H, —CH$_2$—), 6.698~6.730 (d, 1H, J=9.6 Hz, Ar—H), 7.179~7.204 (d, 1H, J=7.5 Hz, Ar—H), 7.494~7.553 (m, 2H, Ar—H), 7.600~7.655 (m, 1H, Ar—H), 7.794 (s, 1H, Ar—H), 8.136~8.168 (dd, 1H, J=1.5 Hz, 8.4 Hz, Ar—H).

Example 17

Preparation of 1-(2-aminobenzyl)-5-(trifluoromethyl)pyridin-2(1H)-one (Compound 17)

The preparation of 1-(2-aminobenzyl)-5-(trifluoromethyl)pyridin-2(1H)-one includes steps of: heating 11.7 g (0.039 mol) of 1-(2-nitrobenzyl)-5-(trifluoromethyl)pyridin-2(1H)-one, 400 mL of 50% ethanol and 6.6 g (0.118 mol) of reductive iron powder to reflux; slowly adding 5 mL of concentrated HCl in 50% ethanol in dropwise way; refluxing for 2 hours under stirring; after reaction, cooling to 50° C.; regulating pH value to 8 by 15% KOH ethanol solution; extracting by ethyl acetate (100+100+50 mL) after evaporating ethanol from the filtrate to half volume; drying the organic phase by anhydrous sodium sulfate; filtering; and evaporating filtrate to the volume of 20 ml, to obtain the crystal product of 1-(2-aminobenzyl)-5-(trifluoromethyl)pyridin-2(1H)-one. The product is light-yellow solid. m.p.: 83.4~85.3° C. EI-MS (m/z): 268[M]$^+$. $^1$H-NMR (CDCl$_3$, 300 MHz): δ ppm 5.098 (s, 2H, —CH$_2$—), 6.656~6.687 (d, 1H, J=9.3 Hz, Ar—H), 6.724~6.749 (d, 1H, J=7.5 Hz, Ar—H), 6.770~6.795 (d, 1H, J=7.5 Hz, Ar—H), 7.164~7.208 (m, 2H, Ar—H), 7.431-7.472 (dd, 1H, J=2.7 Hz, 9.6 Hz, Ar—H), 7.755 (s, 1H, Ar—H).

Example 18

Preparation of 1-(3-chlorobenzyl)-5-(trifluoromethyl)pyridin-2(1H)-one (Compound 18)

The preparation of 1-(3-chlorobenzyl)-5-(trifluoromethyl) pyridin-2(1H)-one includes steps of: dissolving 0.49 g (3.0 mmol) of 5-(trifluoromethyl)pyridin-2(1H)-one in 20 ml of DMF; adding 0.66 g (4.8 mmol) of sodium carbonate and 0.93 g (4.5 mmol) 1-(bromomethyl)-3-chlorobenzene; carrying out refluxing reaction for 3 hours; adding 40 ml of 15% ammonia solution; extracting by ethyl acetate (30+20+20 mL); drying by anhydrous sodium sulfate; filtering; evaporating filtrate; and separating residue by column chromatography with eluent of petroleum ether and ethyl acetate with proportion of 6:1 to obtain 0.70 g of the product 1-(3-chlorobenzyl)-5-(trifluoromethyl)pyridin-2(1H)-one as a colorless oil. EI-MS (m/z): 287[M]$^+$. $^1$H-NMR (CDCl$_3$, 300 MHz) δ ppm: 5.098 (s, 2H, —CH$_2$—), 6.656~6.687 (d, 1H, J=9.3 Hz, Ar—H), 7.186~7.210 (m, 1H, Ar—H), 7.307~7.324 (m, 3H, Ar—H), 7.442~7.482 (dd, 1H, J=2.4 Hz, 9.6 Hz, Ar—H), 7.650 (s, 1H, Ar—H).

Example 19

Preparation of 1-(4-methoxybenzyl)-5-(trifluoromethyl)pyridin-2(1H)-one (Compound 19)

The preparation of 1-(4-methoxybenzyl)-5-(trifluoromethyl)pyridin-2(1H)-one includes steps of: dissolving 0.50 g (3.0 mmol) of 5-(trifluoromethyl)pyridin-2(1H)-one in 20 ml of DMF; adding 0.66 g (4.8 mmol) of sodium carbonate and 0.91 g (4.5 mmol) 1-(bromomethyl)-4-methoxybenzene; carrying out refluxing reaction for 3 hours; adding 40 mL of 15% ammonia solution; extracting by ethyl acetate (30+20+20 mL); drying by anhydrous sodium sulfate; filtering; evaporating filtrate; and separating residue by column chromatography with eluent of petroleum ether and ethyl acetate with proportion of 8:1 to obtain 0.79 g of the product 1-(4-methoxybenzyl)-5-(trifluoromethyl)pyridin-2(1H)-one as a white solid. m.p.: 84.2~86.1° C. EI-MS (m/z): 283[M]$^+$. $^1$H-NMR (CDCl$_3$, 300 MHz): δ ppm: 3.806 (s, 3H, —CH$_3$), 5.077 (s, 2H, —CH$_2$—), 6.638~6.670 (d, 1H, J=9.6 Hz, Ar—H), 6.885~6.891 (d, 1H, J=18 Hz, Ar—H), 6.907~6.914 (d, 1H, J=2.1 Hz, Ar—H), 7.259~7.287 (m, 3H, Ar—H), 7.398~7.439 (dd, 1H, J=2.7 Hz, 9.6 Hz, Ar—H), 7.633 (s, 1H, Ar—H).

Example 20

Preparation of 1-(2-fluorobenzyl)-5-(trifluoromethyl)pyridin-2(1H)-one (Compound 20)

The preparation of 1-(3-chlorobenzyl)-5-(trifluoromethyl) pyridin-2(1H)-one includes steps of: dissolving 0.49 g (3.0 mmol) of 5-(trifluoromethyl)pyridin-2(1H)-one in 20 ml of DMF; adding 0.66 g (4.8 mmol) of sodium carbonate and 0.85 g (4.5 mmol) 1-(bromomethyl)-2-fluorobenzene; carrying out refluxing reaction for 3 hours; adding 40 ml of 15% ammonia solution; extracting by ethyl acetate (30+20+20 mL); drying by anhydrous sodium sulfate; filtering; evaporating filtrate; and separating residue by column chromatography with eluent of petroleum ether and ethyl acetate with proportion of 6:1 to obtain 0.65 of the product 1-(2-fluorobenzyl)-5-(trifluoromethyl)pyridin-2(1H)-one as a colorless oil. EI-MS (m/z): 271[M]$^+$. $^1$H-NMR (CDCl$_3$, 300 MHz): δ ppm: 5.176 (s, 2H, —CH$_2$—), 6.623~6.655 (d, 1H, J=9, 6 Hz, Ar—H), 7.074~7.178 (m, 2H, Ar—H), 7.301~7.377 (m, 1H, Ar—H), 7.410~7.505 (m, 2H, Ar—H), 7.795 (s, 1H, Ar—H).

Example 21

Preparation of 1-(2-(2-hydroxyethylamino)benzyl)-5-(trifluoromethyl)pyridin-2(1H)-one

(Compound 21)

The preparation of 1-(2-(2-hydroxyethylamino)benzyl)-5-(trifluoromethyl)pyridin-2(1H)-one includes steps of adding 100 mL of n-butanol to dissolve 9.0 g (0.034 mol) of 1-(2-amino-benzyl)-5-(trifluoromethyl)pyridin-2(1H)-one; adding 4.69 g (0.034 mol) of potassium carbonate and 4.1 g (0.05 mol) of chloroethanol and allowing the resulting system to react at 130° C. for 18 hours under stirring; filtering; evaporating filtrate to dryness; and separating residue by column chromatography with eluent of petroleum ether and ethyl acetate with pro portion of 5:1 to obtain 0.5 g of 1-(2-(2-hydroxyethylamino)benzyl)-5-(trifluoromethyl)pyridin-2(1H)-one as a white solid. m.p.: 114.0~115.0° C. EI-MS (m/z): 312[M]⁺. ¹H-NMR (CDCl₃, 300 MHz): δ ppm: 2.822 (s, 1H, —OH), 3.228~3.261 (t, 2H, —CH₂—), 3.878 (s, 2H, —CH₂—), 5.109 (s, 2H, —CH₂—), 5.843 (br, 1H, —NH—), 6.620~6.647 (d, 1H, Ar—H), 6.686~6.736 (m, 2H, Ar—H), 7.206~7.303 (m, 2H, Ar—H), 7.458~7.499 (dd, 1H, J=2.7 Hz, 9.6 Hz, Ar—H), 7.802 (s, 1H, Ar—H).

Example 22

Preparation of 1-(2-(2-(piperazin-1-yl)ethylamino)benzyl)-5-(trifluoromethyl)pyridin-2(1H)-one (Compound 22)

A. Preparation of 1-(2-((2-chloroethyl)amino)benzyl)-5-(trifluoromethyl)pyridin-2(1H)-one

The preparation of 1-(2-((2-chloroethyl)amino)benzyl)-5-(trifluoromethyl)pyridin-2(1H)-one includes steps of: dissolving 2.2 g of 1-(2-((2-hydroxyethyl)amino)benzyl)-5-(trifluoromethyl)pyridin-2(1H)-one by 40 ml of dichloromethane; adding 1.7 g of sulfurous dichloride and 1.2 g of triethylamine; allowing the resulting system to react at room temperature for 10 hours under stirring; and separating residue by column chromatography to obtain 1.5 g of white solid. m.p.: 93.5~95.0° C. EI-MS (m/z): 330[M]⁺. ¹H-NMR (CDCl₃, 300 MHz): δ ppm: 3.483~3.543 (t, 2H, —CH₂—), 3.628~3.672 (t, 2H, —CH₂—), 5.089 (s, 2H, —CH₂—), 5.737~5.753 (1H, —NH—), 6.618~6.757 (m, 3H, Ar—H), 7.206~7.235 (dd, 1H, J=1.2 Hz, 7.5 Hz, Ar—H), 7.250~7.307 (dd, 1H, J=8.1 Hz, 9.0 Hz, Ar—H), 7.732 (s, 1H, Ar—H).

B. Preparation of 1-(2-(2-(piperazin-1-yl)ethylaminof)benzyl)-5-(trifluoromethyl)pyridin-2(1H)-one The preparation of 1-(2-(2-(piperazin-1-yl)ethylaminof)benzyl)-5-(trifluoromethyl)pyridin-2(1H)-one includes steps of: dissolving 0.33 g (1 mmol) of 1-(2-((2-chloroethyl)amino)benz yl)-5-(trifluoromethyl)pyridin-2(1H)-one in 20 mL of acetonitrile; adding 0.53 g (6 mmol) of anhydrous piperazine and a catalytic amount of sodium iodide; carrying out refluxing reaction for 20 hours; filtering; evaporating filtrate to dryness; and separating by column chromatography with methanol to obtain 0.26 g of yellow oil. EI-MS (m/z): 380[M]⁺. ¹H-NMR (CDCl₃, 300 MHz): δ ppm: 2.434 (s, 4H, —CH₂—), 2.575~2.615 (t, 2H, —CH₂—), 2.839~2.853 (d, 4H, —CH₂—), 3.181~3.200 (d, 2H, —CH₂—), 5.153 (s, 2H, —CH₂—), 5.275 (s, 1H, —NH—), 6.636~6.740 (m, 3H, Ar—H), 7.150~7.174 (d, 1H, J=7.2 Hz, Ar—H), 7.283~7.309 (m, 1H, Ar—H), 7.426~7.458 (d, 1H, J=9.6 Hz, Ar—H), 7.632 (s, 1H, Ar—H).

Example 23

Preparation of 1-(2-(2-(4-methylpiperazin-1-yl)ethylamino)benzyl)-5-(trifluoromethyl)pyridin-2(1H)-one (Compound 23)

The preparation of 1-(2-(2-(4-methylpiperazin-1-yl)ethylamino)benzyl)-5-(trifluoromethyl)pyridin-2(1H)-one includes steps of: dissolving 0.33 g (1 mmol) of 1-(2-((2-chloroethyl)amino)benzyl)-5-(trifluoromethyl)pyridin-2(1H)-one in 20 mL of acetonitrile; adding 0.55 g (5 mmol) of 1-methylpiperazine and a catalytic amount of sodium iodide; carrying out refluxing reaction for 20 hours; filtering; evaporating filtrate to dryness; and separating by column chromatography with ethyl acetate (2% triethylamine) to obtain 0.28 g of the product 1-(2-(2-(4-methylpiperazin-1-yl)ethylamino)benzyl)-5-(trifluoromethyl)pyridin-2(1H)-one as a yellow oil. ESI-MS (m/z): 395[M+H]⁺. ¹H-NMR (CDCl₃, 300 MHz): δ ppm: 2.308 (s, 3H, —CH₃), 2.526 (br, 8H, —CH₂—), 2.603~2.645 (t, 2H, —CH₂—), 3.159~3.216 (m, 2H, —CH₂—), 5.059 (s, 2H, —CH₂—), 5.148 (s, 1H, —NH—), 6.364~6.742 (m, 3H, Ar—H), 7.157~7.175 (d, 1H, J=7.2 Hz, Ar—H), 7.284~7.301 (1H, Ar—H), 7.423~7.462 (dd, 1H, J=2.4 Hz, 9.3 Hz, Ar—H), 7.631 (s, 1H, Ar—H).

Example 24

Preparation of 1-(2-acetamide-benzyl)-5-(trifluoromethyl)pyridin-2(1H)-one (Compound 24)

The preparation of 1-(2-acetamide-benzyl)-5-(trifluoromethyl)pyridin-2(1H)-one includes steps of: dissolving 1.1 mol of acetic anhydride and 0.32 g (1 mmol) of 1-(2-aminobenzyl)-5-(trifluoromethyl)pyridin-2(1H)-one in 20 ml of acetic acid; carrying out refluxing reaction for 2 hours; adding 20 ml of water and extracting by ethyl ether (2*20 mL); washing the organic phase with 15% sodium bicarbonate solution and drying the organic phase by anhydrous sodium sulfate; filtering; and evaporating filtrate; and separating residue by column chromatography with eluent of petroleum ether and ethyl acetate with proportion of 3:1 to obtain 0.20 g of a white solid. m.p.: 183.0~185.0° C. ESI-MS (m/z): 333 [+Na]⁺. ¹H-NMR (CDCl₃, 300 MHz) δ ppm: 2.280 (s, 3H—CH₃), 5.113 (s, 2H, —CH₂—), 6.703~6.735 (d, 1H, J=9.6 Hz, Ar—H), 7.114~7.163 (t, 1H, Ar—H), 7.338~7.424 (m, 2H, Ar—H), 7.516~7.543 (dd, 1H, J=2.4 Hz, 9.3 Hz, Ar—H), 7.904 (s, 1H, Ar—H), 8.143~8.170 (d, 1H, J=8.1 Hz, Ar—H), 9.975 (s, 1H, —NH—).

Example 25

Preparation of 1-(2-(2-morpholino ethylamino)benzyl)-5-(trifluoromethyl)pyridin-2(1H)-one

(Compound 25)

The preparation of 1-(2-(2-morpholinoethylamino)benzyl)-5-(trifluoromethyl)pyridin-2(1H)-one includes steps of: dissolving 0.26 g (0.79 mmol) of 1-(2-((2-chloroethyl)amino)benzyl)-5-(trifluoromethyl)pyridin-2(1H)-one in 20 mL of acetonitrile; adding 1.0 g (11.5 mmol) of morpholine and a catalytic amount of sodium iodide; carrying out refluxing reaction for 25 hours; filtering; evaporating filtrate to dryness; dissolving the residue with ethyl acetate and washing with water; drying the organic phase by anhydrous sodium sulfate; and separating by column chromatography with eluent of petroleum ether and ethyl acetate with proportion of 1:1 to obtain 0.18 of the product 1-(2-(2-morpholinoethylamino)benzyl)-5-(trifluoromethyl)pyridin-2(1H)-one as an off-white solid. m.p.: 101.0~103.0° C. EI-MS (m/z): 381[M]$^+$. $^1$H-NMR (CDCl$_3$, 300 MHz): δ ppm: 2.472 (s, 4H, —CH$_2$—), 2.616 (s, 2H, —CH$_2$—), 3.201 (s, 2H, —CH$_2$—), 3.685 (s, 4H, —CH$_2$—), 5.071 (s, 2H, —CH$_2$—), 5.179 (s, 1H, —NH—), 6.633~6.746 (m, 3H, Ar—H), 7.163~7.187 (d, 1H, J=7.2 Hz, Ar—H), 7.285~7.311 (1H, Ar—H), 7.423~7.463 (dd, 1H, J=2.4 Hz, 9.6 Hz, Ar—H), 7.643 (s, 1H, Ar—H).

Example 26

Preparation of 1-(4-(2-(2-hydroxyethoxy)ethylamino)benzyl)-5-(trifluoromethyl)pyridin-2(1H)-one The preparation of 1-(4-(2-(2-hydroxyethoxy)ethylamino)benzyl)-5-(trifluoromethyl)pyridin-2(1H)-one includes steps of dissolving 1-(4-((2-chloroethyl)amino)benzyl)-5-(trifluoromethyl)pyridin-2(1H)-one and 0.37 g (3 mmol) of chloroethoxy ethanol in 20 mL of normal butanol; adding 0.28 g (2 mmol) of potassium carbonate and a catalytic amount of sodium iodide; carrying out refluxing reaction for 28 hours; after reaction, filtering; evaporating filtrate to dryness; and separating by column chromatography with eluent of petroleum ether and ethyl acetate with proportion of 2:1 to obtain 0.22 g of yellow oily product. EI-MS (m/z): 356[M]$^+$. $^1$H-NMR (CDCl$_3$, 300 MHz) δ ppm: 3.312~3.346 (t, 2H, —CH$_2$—), 3.589~3.619 (t, 2H, —CH$_2$—), 3.652~3.776 (t, 4H, —CH$_2$—), 5.019 (s, 2H, —CH$_2$—), 6.623~6.679 (t, 3H, Ar—H), 7.154~7.182 (d, 2H, Ar—H), 7.384~7.425 (dd, 1H, J=2.7 Hz, 9.6 Hz, Ar—H), 7.619 (s, 1H, Ar—H).

Example 27

Inhibition Test of Compounds on NIH3T3 fibroblasts

An MTT method is used and comprises steps of: culturing cells in DMEM culture medium including 5% calf serum and preparing the cells into cell suspension of $3 \times 10^4$/ml; inoculating in 96-well plate according to 100 µl/well; transferring new culture medium including compounds with different concentration, fluorofenidone and 1% calf serum after cells are adhered, wherein three repeated wells are provided for each concentration; respectively adding 100 µl of MTT solution in each well after 48 hours and 72 hours of administrating (the culture medium is prepared into 5 mg/ml and kept in dark after filtering), sucking out MTT after 4 hours; adding 150 µl of DMSO which is the dissolving liquid of MTT; after 10 min and MTT is completely dissolved, measuring OD value by ELISA reader; calculating IC50 values of fluorofenidone and measured compounds according to inhibition ratio; calculating multiple of activities of measured compounds and fluorofenidone according to IC50 values of fluorofenidone and measured compounds; and obtaining relative IC50 value of measured compounds according to multiple and IC50 value of fluorofenidone on a certain plate.

| Inhibition activity of measured compounds to NIH3T3 mechanocyte | | | | |
|---|---|---|---|---|
| | 48 hours | | 72 hours | |
| Measured compounds | Relative IC$_{50}$ (mM) | Multiple | Relative IC$_{50}$ (mM) | Multiple |
| Fluorofenidone | 4.43 | — | 3.52 | — |
| Structure IV | 1.160 | 3.82 | 0.729 | 4.83 |
| Compound 1 | 0.552 | 8.03 | 0.470 | 7.50 |
| Compound 2 | 1.393 | 3.18 | 1.511 | 2.33 |
| Compound 3 | 0.424 | 10.46 | 0.229 | 15.39 |
| Compound 4 | 0.957 | 4.63 | 0.144 | 24.43 |
| Compound 5 | 0.141 | 31.39 | 0.098 | 35.83 |
| Compound 6 | 1.011 | 4.38 | 0.638 | 5.51 |
| Compound 7 | 4.179 | 1.06 | 0.340 | 10.36 |
| Compound 8 | 0.367 | 12.07 | 0.229 | 15.36 |
| Compound 9 | 0.181 | 24.53 | 0.120 | 29.38 |
| Compound 11 | 0.526 | 8.42 | 0.131 | 26.88 |
| Compound 13 | 0.128 | 34.55 | 0.068 | 52.14 |
| Compound 14 | 0.346 | 12.81 | 0.182 | 19.29 |
| Compound 15 | 1.078 | 4.11 | 1.093 | 3.22 |
| Compound 16 | 1.035 | 4.28 | 1.032 | 3.41 |
| Compound 17 | 1.808 | 2.45 | 1.271 | 2.77 |
| Compound 18 | 1.457 | 3.04 | 1.349 | 2.61 |
| Compound 19 | 0.301 | 14.72 | 0.384 | 9.16 |
| Compound 20 | 0.273 | 16.25 | 0.393 | 8.95 |
| Compound 21 | 0.664 | 6.67 | 0.587 | 6.00 |
| Compound 22 | 0.168 | 26.31 | 0.291 | 12.10 |
| Compound 25 | 0.368 | 12.04 | 0.264 | 13.33 |

Notes:
multiple is IC$_{50}$ value of compounds to IC$_{50}$ value of fluorofenidone

Example 28

Observation of Treatment Effect of Compound 13 in a Rat Unilateral Ureteral Obstruction Renal Fibrosis Model Materials and Methods 1. Experimental Chemicals The compound 13 is prepared according to the method provided by the invention.

2. Experimental Animals

Nine male SD rats of 188-213 g, coming from Hunan Slac Laboratory Animals Co., Ltd., are illuminated for 12 hours every day; feed is provided by Shanghai Slac Laboratory Animals Co., Ltd.; and drinking water is provided by Department of Laboratory Animal Science of Central South University.

3. Experimental Methods (1) Randomization: nine rats are divided into three groups at random, namely a normal group (n=3); a model group (n=3) and a treatment group (n=3) treated by compound 13 of 15 mg/kg; three rats are in a hutch; and the experimental animals are adaptively fed for two days.

(2) Unilateral Ureteral Obstruction Modeling:

The unilateral ureteral obstruction modeling comprises steps of: lumbar-injecting each rat with 10% chloral hydrate according to 0.35 ml/100 g for anesthesia, fixing on a rat fixing plate; wetting the back skin with water, tightening the skin; shaving by elbowed surgical scissors close to the skin; sterilizing drape in a conventional way; making an incision of 1.0 cm in longitudinal direction at a junction of a position 1.0 cm below left costal margin and 0.8 cm next to median line of vertebral column; separating successive layers to expose left kidney and left ureter; tying off left ureter against lower pole of left kidney by a thread of 4.0 and another portion 1.0 cm therebelow; isolating ureter between those two points; flushing abdominal cavity by gentamicin physiological saline solution; and stitching successive layers of retroperitoneal space and back skins after no leakage and hemorrhage.

(3) Pharmacological intervention: intragastric administration is carried out the day before modeling operation according to one time per day for 12 days; the method is detailed as follows:

a) preparing 0.5% CMCNa solution by adding an amount of 0.9% physiological saline into CMCNa powder and preparing following samples with 0.5% CMCNa solution as solvent.

b) lavaging the normal group using 6 ml/kg.d of 0.5% CMCNa for one time per day.

c) lavaging the model group using 6 ml/kg.d of 0.5% CMCNa for one time per day.

d) lavaging the treatment group treated with compound 13 at 15 mg/kg using 6 ml/kg.d 0.5% CMCNa for one time per day.

(4) Animal Sacrifice and Sample Collection

On the $11^{th}$ day after operation, each group of rats is respectively sacrificed by lumbar injection of 10% chloral hydrate (0.7-0.9 ml/100 g) to excessive anesthesia, renal tissues on the obstruction side are fixed by 4% formaldehyde, embedded in paraffin and prepared into 4 µm-thick slices for HE staining and Masson staining.

(5) HE Staining Evaluation Standard:

HE stained slices of renal tissues are successively observed in fives fields of view of renal tubulointerstitium on upper left side, upper right side, lower left side, lower right side and middle portion by a low power lens and are evaluated according to eight indexes of renal interstitium lesion: renal tubular epithelial cell vacuolar degeneration, renal tubular ectasia, renal tubular atrophy, red cell cast, protein cast, interstitial edema, interstitial fibrosis and interstitial inflammatory cell infiltration; an average value is calculated as the index of renal tubulointerstitial lesion of the sample; and the evaluation standard is based on the reference of Radford M G Jr, Donadio J V Jr, Bergstralh E J, et al. Predicting renal outcome in IgA nephropathy. J Am Soc Nephrol, 1997, 8(2):199-207.

(6) Masson Staining Evaluation Standard

Masson stained slices of renal tissues are observed in 20 fields of vision for each sample at random under 400× light microscope; percent of blue-stained collagens in the fields of vision is calculated; an average value is determined after semi-quantitative evaluation: no positive staining, 0; <25%, 1; 25-50%, 2; 50-75%, 3; >75%, 4; and the evaluation standard is based on references.

4. Statistical Methods: analytical method of variance of single factor is adopted.

Experimental Results

1. Pathological Evaluation Results of Renal Interstitium Lesions Through HE Staining

TABLE 1 comparison of indexes of renal tubulointerstitial lesions of obstruction kidneys of rats in groups

| Group | Number | Score($\bar{X} \pm S$) |
|---|---|---|
| Normal group | 3 | $0.33 \pm 0.12$ |
| Model group | 3 | $9.00 \pm 1.00^{\star\star\star}$ |
| Compound 13 group | 3 | $7.00 \pm 0.35^{\star\star\star\ast\ast}$ |

Notes:

comparison to normal group, $^{\star}p < 0.05$, $^{\star\star}p < 0.01$; $^{\star\star\star}p < 0.001$;

comparison to model group, $^{*}p < 0.05$, $^{}p < 0.01$, $^{*}p < 0.001$;

2. Pathological Evaluation Results of Renal Interstitium Lesions Through MASSON Staining

TABLE 2 evaluation results of renal interstitium collagens of left kidneys of rats in groups through MASSON staining

| Group | Number | Score($\bar{X} \pm S$) |
|---|---|---|
| Normal group | 3 | $0.25 \pm 0.00$ |
| Model group | 3 | $2.45 \pm 0.38^{\star\star\star}$ |
| Compound 13 group | 3 | $1.52 \pm 0.16^{\star\star\star\ast\ast}$ |

Notes:

comparison to normal group, $^{\star}p < 0.05$, $^{\star\star}p < 0.01$; $^{\star\star\star}p < 0.001$;

comparison to model group, $^{*}p < 0.05$, $^{}p < 0.01$, $^{*}p < 0.001$;

Conclusion

The compound 13 at 15 mg/kg can effectively treat renal fibrosis.

The invention claimed is:

1. A 1-(substituted benzyl)-5-trifluoromethyl-2(1H)pyridone compound, having a structural formula (XIII), Structural formula XIII:

Structural formula XIII wherein R1-R4 and R12 are selected from H, CN, $NO_2$, hydroxyl, amino, a halogen atom, $C_1$-$C_6$ alkoxyl, $NR^{10}R^{11}$, $OR^{13}$, $C(O)R^{14}$, O—$C(O)R^{14}$, $C_1$-$C_6$ alkyl, $C_1$-$C_6$ haloalkyl, $C_2$-$C_6$ alkenyl and a carboxylic ester; wherein R1-R4 and R12 are not simultaneously H, $R^{14}$ is selected from $C_1$-$C_6$ alkyl;
wherein $OR^{13}$ is selected from hydroxyalkyl or alkoxyalkyl;
wherein in $NR^{10}R^{11}$, $R^{10}$ and $R^{11}$ are selected from H, $C_1$-$C_6$hydroxyalkyl, esterified $C_1$-$C_6$-hydroxyalkyl, $C_1$-$C_6$ alkoxyalkyl, or structural formula XIV,
Structural formula XIV:

Structural formula XIV wherein in structural formula XIV, R5 is selected from H, $C_1$-$C_6$ alkyl, $C_1$-$C_6$ haloalkyl, $C_1$-$C_6$ hydroxyalkyl, and $C_2$-$C_6$ alkenyl; R6-R9 are selected from H, $C_1$-$C_6$ alkoxy, =O, $C_1$-$C_4$ alkyl, $C_1$-$C_4$ haloalkyl, $C_1$-$C_4$ hydroxyalkyl, and $C_2$-$C_4$ alkenyl; X is selected from N and CH; Y is selected from N, O, and C, wherein when Y is O, R5 is absent; and n is 1-6; and pharmaceutically acceptable salts thereof.

2. The 1-(substituted benzyl)-5-trifluoromethyl-2(1H)pyridone compound according to claim 1, wherein the pharmaceutically acceptable salts are hydrochlorate, sulfate, phosphate, perchlorate, methanesulfonate, trifluoromethanesulfonate, formate, acetate, propionate, butyrate, maleate, succinate, trifluoroacetate, succinate, salicylate, DL-aspartate, D-aspartate, L-aspartate, DL-glutamate, D-glutamate, L-glutamate, glycerate, succinate, stearate, DL-tartrate, D-tartrate, L-tartrate, (+/−)-mandelate, (R)-(−)-mandelate, (S)-(+)-mandelate, citrate, mucate, maleate, malonate, benzoate, DL-malate, D-malate, L-malate, hemimalate, 1-adamantane acetate, 1-adamantane carboxylate, flavianate, sulfoacetate, (+/−)-lactate, L-(+)-lactate, D-(−)-lactate, pamoate, D-α-galacturonic acid salt, glycerate, DL-cystine salt, D-cystine salt, L-cystine salt, DL-homocystine salt, D-homocystine salt, L-homocystine salt, DL-cysteine salt, D-cysteine salt, L-cysteine salt, (4S)-hydroxy-L-proline, cyclopropane-1,1-dicarboxylate, 2,2-methyl malonate, tyrosine salt, proline salt, fumarate, 1-hydroxy-2-naphthoate, phosphonoacetate, carbonate, bicarbonate, 3-phosphonopropionate, DL-pyroglutamate, D-pyroglutamate, L-pyroglutamate, toluenesulfonate, benzenesulfonate, esilate, (+/−)-camsilate, naphthalenesulfenesulfonate, 1R-(−)-camsilate, 1S-(+)-camsilate, 1,5-napadisilate, 1,2-ethanedisulphonate, 1,3-propanedisulphonate, 3-(N-morpholino) propane sulphonate, biphenyl sulphonate, isethionate, 1-hydroxy-2-naphthalenesulfenesulfonate, dihydric phosphate, potassium hydrogen phosphate, dipotassium phosphate, potassium phosphate, sodium hydrogen phosphate, disodium phosphate, sodium phosphate, sodium dihydrogen phosphate, calcium phosphate, tertiary calcium phosphate, hexafluoro phosphate, ethenyl phosphate, 2-carboxylethyl phosphate or phenyl phosphate.

3. The 1-(substituted benzyl)-5-trifluoromethyl-2(1H)pyridone compound according to claim 1, wherein one of R1-R4 and R12 is $NR^{10}R^{11}$ or $OR^{13}$.

4. The 1-(substituted benzyl)-5-trifluoromethyl-2(1H)pyridone compound according to claim 1, wherein when one of R1-R4 and R12 is $NR^{10}R^{11}$ or $OR^{13}$, then the others are H.

5. A 1-(substituted benzyl)-5-trifluoromethyl-2(1H)pyridone compound according to claim 1, wherein the compound is selected from the group consisting of:
1-(4-nitrobenzyl)-5-(trifluoromethyl)pyridin-2(1H)-one;
1-(4-amino-benzyl)-5-(trifluoromethyl)pyridin-2(1H)-one;
1-(44(3-morpholinylpropyl)amino)benzyl)-5-(trifluoromethyl)pyridin-2(1H)-one;
1-(4-(((3-piperidin-1-yl)propyl)amino)benzyl)-5-(trifluoromethyl)pyridin-2(1H)-one;
1-(4-((3-(4-methyl-piperazin-1-yl)propyl)amino)benzyl)-5-(trifluoromethyl)pyridin-2(1H)-one;
1-(4-((2-hydroxyethyl)amino)benzyl)-5-(trifluoromethyl)pyridin-2(1H)-one;
1-(4-((2-(piperidyl-1-yl)ethyl)amino)benzyl)-5-(trifluoromethyl)pyridin-2(1H)-one;
1-(4-((2-morpholinylethyl)amino)benzyl)-5-(trifluoromethyl)pyridin-2(1H)-one;
1-(4-((2-(4-methyl-piperazin-1-yl)ethyl)amino)benzyl)-5-(trifluoromethyl)pyridin-2(1H)-one;
1-(4-((2-(piperazin-1-yl)ethyl)amino)benzyl)-5-(trifluoromethyl)pyridin-2(1H)-one;
1-(4-((2-(4-(2-hydroxyethyl)piperazin-1-yl)ethyl)amino)benzyl)-5-(trifluoromethyl)pyridine-2(1H)-one;
1-(4-((2-(4-methyl-piperazin-1-yl)ethyl)amino)benzyl)-5-(trifluoromethyl)pyridin-2(1H)-one dihydrochloride;
1-(4-acetamide-benzyl)-5-(trifluoromethyl)pyridin-2(1H)-one;
1-(2,6-dichlorobenzyl)-5-(trifluoromethyl)pyridin-2(1H)-one;
1-(4-fluorobenzyl)-5-(trifluoromethyl)pyridin-2(1H)-one;
1-(2-nitrobenzyl)-5-(trifluoromethyl)pyridin-2(1H)-one;
1-(2-aminobenzyl)-5-(trifluoromethyl)pyridin-2(1H)-one;
1-(3-chlorobenzyl)-5-(trifluoromethyl)pyridin-2(1H)-one;
1-(4-methoxybenzyl)-5-(trifluoromethyl)pyridin-2(1H)-one;
1-(2-fluorobenzyl)-5-(trifluoromethyl)pyridin-2(1H)-one;
1-(2-(2-hydroxyethylamino)benzyl)-5-(trifluoromethyl)pyridin-2(1H)-one;
1-(2-(2-(piperazin-1-yl)ethylaminof)benzyl)-5-(trifluoromethyl)pyridin-2(1H)-one;
1-(2-(2-(4-methylpiperazin-1-yl)ethylamino)benzyl)-5-(trifluoromethyl)pyridin-2(1H)-one;

1-(2-acetamide-benzyl)-5-(trifluoromethyl)pyridin-2 (1H)-one;

1-(2-(2-morpholinoethylamino)benzyl)-5-(trifluoromethyl)pyridin-2-(1H)-one; and 1-(4-(2-(2-hydroxyethoxy)ethylamino)benzyl)-5-(trifluoromethyl)pyridin-2(1H)-one.

6. An anti-fibrosis medicament comprising a compound described in any one of claims 1-5 and a pharmaceutically acceptable excipient.

* * * * *